United States Patent [19]

Moore

[11] 4,014,903
[45] Mar. 29, 1977

[54] RECOVERY OF DICARBOXYLIC ACIDS FROM AQUEOUS SOLUTION CONTAINING NITRIC ACID

[75] Inventor: William Percy Moore, Hopewell, Va.

[73] Assignee: Allied Chemical Corporation, Morris Township, N.J.

[22] Filed: Aug. 11, 1975

[21] Appl. No.: 603,829

[52] U.S. Cl. .............................. 260/345.9; 203/79; 203/91; 203/96; 260/537 R; 260/346.8 R
[51] Int. Cl.² .......................................... B01D 3/38
[58] Field of Search ................. 203/13, 28, 48, 81, 203/96, 79; 260/537 R, 537 P, 346.4, 346.8 A, 346.8 R, 345.9

[56] References Cited

UNITED STATES PATENTS

| 3,354,056 | 11/1967 | Wegerich | 203/48 |
|---|---|---|---|
| 3,359,283 | 12/1967 | Campbell | 203/91 |
| 3,657,280 | 4/1972 | Lese | 203/48 |
| 3,758,564 | 9/1973 | Davis | 260/537 P |

*Primary Examiner*—Hiram H. Bernstein
*Attorney, Agent, or Firm*—Fred L. Kelly

[57] ABSTRACT

A process for treating an adipic acid bleed stream obtained in the manufacture of adipic acid, said adipic acid bleed stream consisting mainly of nitric, adipic, glutaric, and succinic acids and a catalyst; the process comprising maintaining said adipic acid bleed stream in aqueous solution, and stripping nitric acid from said aqueous solution with steam at a temperature of about 100°–110° C. while maintaining in said aqueous solution a water to nitric acid weight ratio of at least 6, to remove substantially all of the nitric acid therefrom, thereby forming an aqueous nitric acid free mixture of said dibasic acids and said catalyst which can be safely dehydrated and distilled to produce useful chemicals.

4 Claims, No Drawings

4,014,903

RECOVERY OF DICARBOXYLIC ACIDS FROM AQUEOUS SOLUTION CONTAINING NITRIC ACID

BACKGROUND OF THE INVENTION

This invention relates to a process for the recovery of organic dibasic acids from an aqueous acid solution containing nitric acid. More particularly, the present invention relates to a process for the recovery of useful chemicals from an adipic acid bleed stream containing nitric acid, adipic acid, glutaric acid, succinic acid, and an oxidation catalyst, for example copper and vanadium salts.

Adipic acid is a valuable and widely used chemical. A well-known commercial method of producing adipic acid involves oxidizing mixtures of cyclohexanol and cyclohexanone with nitric acid in the presence of a catalyst, for example, a mixture of copper and vanadium salts. As a by-product of the process there is obtained an aqueous mixture of dicarboxylic acids containing mainly adipic acid, glutaric acid, succinic acid, nitric acid and catalyst. This by-product mixture is taken as a bleed stream on the adipic acid process primarily for the removal of organic acids having less than six carbon atoms. Difficulties have hitherto been encountered in purifying this adipic acid bleed stream and it is usually wasted, causing a formidable environmental problem.

U.S. Pat. No. 3,359,283 issued Dec. 19, 1967, to Campbell et al., is directed to a process of treating a mixture of organic dibasic acids including succinic acid, glutaric acid, and adipic acid, which comprises the steps of heating said mixture at a temperature of at least 190° C. under a reduced pressure for a time sufficient to dehydrate the succinic acid to succinic anhydride, distilling the so-produced succinic anhydride together with the water of dehydration, and recovering the succinic anhydride from the make of the distillation. The patent further discloses that nitric acid present in the crude mixture of organic dibasic acids can be distilled by passing the mixture through a steam still at a temperature between 90° and 150° C. and at a pressure of 10 to 400 mm. of Hg, wherein much of the nitric acid and water is passed overhead. The removal of nitric acid is continued without complete evaporation to dryness taking place until a pH after dilution of at least 1.2 but preferably not greater than 2.2 is obtained.

Although the process of U.S. Pat. No. 3,359,283 is of major interest in this art, I have found that low pressure distillation of nitric acid from the organic dibasic acids is relatively expensive and not very efficient in terms of nitric acid distillation. Moreover, runaway reaction of the nitric acid with the organic dibasic acids may occur if the nitric acid is not efficiently and completely removed from the concentrated reaction mixture. Accordingly, I have carried out considerable research to discover a process whereby nitric acid may be safely and efficiently distilled from organic dibasic acids.

SUMMARY OF THE INVENTION

In accordance with the present invention, I provide a process for treating an adipic acid bleed stream obtained in manufacture of adipic acid by oxidizing with nitric acid a mixture of cyclohexanol and cyclohexanone in the presence of a catalyst consisting of a mixture of copper and vanadium salts, said adipic acid bleed stream consisting mainly of nitric, adipic, glutaric, and succinic acids and said catalyst; the process comprising maintaining said adipic acid bleed stream in aqueous solution, and stripping nitric acid from said aqueous solution with steam at a temperature of about 100°–110° C. while maintaining in said aqueous solution a water to nitric acid weight ratio of at least 6, to remove substantially all of the nitric acid therefrom, thereby forming an aqueous nitric acid free mixture of said dibasic acids and said catalyst which can be safely dehydrated and distilled to produce useful chemicals.

DESCRIPTION OF THE PREFERRED EMBODIMENT

In accordance with a preferred embodiment of the present invention, nitric acid, adipic acid, succinic anhydride, glutaric anhydride, and catalyst are recovered from an adipic acid bleed stream having the following representative composition:

|  | Percent by Weight |
|---|---|
| Nitric acid | 10.0 |
| Adipic acid | 10.0 |
| Glutaric acid | 15.0 |
| Succinic acid | 5.0 |
| Other carboxylic acids | 1.0 |
| Cu (NO$_3$)$_2$ | 0.6 |
| V$_2$O$_5$ | 0.1 |
| Water | 58.3 |

Because of the difficulty in further treatment, the adipic acid bleed stream is commonly disposed of as waste, such as by burning the residual organic matter. Obviously, this represents an environmental problem as well as a substantial loss of valuable chemicals.

In order to illustrate the present invention, the following examples are given which exemplify the invention but should not be regarded as limiting the same. The parts and percentages employed are by weight unless otherwise indicated.

EXAMPLE 1

The above-described representative adipic acid bleed stream is received from a plant for the manufacture of adipic acid by oxidizing with nitric acid a mixture of cyclohexanol and cyclohexanone in the presence of a catalyst consisting of copper and vanadium salts. The adipic acid bleed stream is received from the adipic acid plant as a clear, green, liquid, either by tank truck or by pipeline into an insulated stainless steel storage tank. The bleed stream is received at a rate of about 30,000 parts per day at about 60° C. The storage tank contains stainless steel steam coils to prevent cooling and adipic acid precipitation if prolonged storage is required.

About 30,000 parts of bleed solution is normally charged one time per day to a conventional crystallizer called the adipic acid crystallizer, a stirred, stainless steel, insulated vessel containing stainless steel cooling coils. The bleed solution is circulated through the tubes of an external water-cooled tube and shell heat exchanger until temperature of the circulating fluid has been reduced to 30°–45° C. and adipic acid crystallization is about three-fourths complete. Circulation of the slurry is stopped but low speed agitation is continued while circulation of chilled methanol through the crystallizer coils from a refrigeration unit is started. Temperature is reduced to 4°–6° C. and held there for 30 minutes.

The slurry from the crystallizer is charged to a conventional centrifuge, called the adipic acid centrifuge, batchwise. The centrifuge is a stainless steel perforate bowl, underdriven machine with the capacity for handling about 600 parts of adipic acid crystals per loading. When the centrifuge has been loaded, the crystals are rinsed with water, amounting to about the same weight as the crystals loaded on the centrifuge.

The centrifugate and rinse water from the adipic recovery are combined and retained in a stainless steel centrifugate tank which serves as a feed tank for the aqueous nitric acid stripping operation, described hereinafter.

When the adipic acid cake has been loaded and rinsed on the centrifuge, the valving on the centrifugate line is changed to allow the next centrifugate to go to an adipic acid solution tank, a stainless steel tank initially containing nitric acid recovered from the nitric acid distillation, described hereinafter. This recovered nitric acid is circulated from the adipic solution tank through the tube side of a stainless steel external heat exchanger and brought to 70°–80° C. Then the circulating nitric acid solution is allowed to pass into the adipic acid centrifuge operating at full speed. The hot aqueous nitric acid dissolves the purified, damp adipic acid on the centrifuge bowl, and the solution passes through the filtrate line and into the adipic acid solution tank. When the centrifuge bowl is clear, the cycle is repeated. It is desirable to cool the centrifuge bowl with chilled water from the refrigeration unit prior to repeating the cycle. The aqueous nitric acid-adipic solution is allowed to collect in the solution tank and maintained at 60+° C. Recoveries of about 11,000 parts per day of solution containing 20% adipic acid and 25% nitric acids are normal. This product may be returned to the adipic acid plant.

The centrifugate from the above-described centrifugate tank is continuously pumped to the top tray of a conventional stripper called the nitric acid stripper, which contains 3 sieve trays and operates at atmospheric or slightly above atmospheric pressure and at 100° to 110° C. Aqueous nitric acid is stripped from the centrifugate to produce an aqueous nitric acid free mixture of the organic dibasic acids and catalyst. It is important that the dibasic acids are maintained in aqueous solution during the stripping operation. Specifically, at least 10 to 25 percent of water is maintained in said solution by addition of water and/or steam to the stripper as necessary. By operation in this manner, the danger of runaway reaction in the stripper is eliminated. Aqueous nitric acid is stripped from the top tray through a demister and enters the lower portion of a conventional distillation column called the nitric acid distillation column, in the vapor phase. Heat is supplied to the nitric acid stripper primarily by a stainless steel tube and sheel reboiler with the process stream circulated through the tube side of the exchanger. The remaining heat is supplied by the steam injected below the bottom tray of the stripper. The steam is continuously injected to assure that the ratio of water to nitric acid does not get below six parts of water per part of nitric acid in any part of the stripper. Preferably, said ratio of water to nitric acid is maintained above about 8 parts of water per part of nitric acid. An aqueous solution containing primarily dibasic carboxylic acids and catalyst salts is removed via level controlled valve from the circulating line before the heat exchanger, to an aqueous dibasic acid storage tank.

The vapor feed from the nitric acid stripping column enters the nitric acid distillation column at the sixth tray of the stainless steel distillation column containing 16 sieve trays. The column operates at atmospheric pressure with reflux ratio controlled at 0.3/1 to 0.6/1 by an electrically timed tilting cup reflux splitter. Heat is supplied to the column by the hot vapor feed and by a tube and sheel reboiler. Circulation through this reboiler is provided by a stainless steel centrifugal pump, and the column bottoms containing the nitric acid is fed to the adipic acid solution tank by action of the column level control valve. Preferably, overhead temperature is 100° C., reboiler temperature 118° C., and feed tray temperature about 110° C.

Distillate from the nitric acid column contains no more than 0.1% nitric acid. It is sent to an effluent tank for neutralization along with the other process effluents prior to discharge. A very small amount of vapor containing carbon dioxide and traces of nitrogen oxides is discharged from the nitric acid column condenser and is sent to a urea liquor scrubber for treatment prior to discharge to the atmosphere.

The aqueous dibasic acids recovered from the nitric acid stripper are stored in a dibasic acid storage tank. This material contains about 55% glutaric acid, 19% succinic acid, 13% water, 8% adipic acid and 3% catalyst salts, and is used as the source of chemical values to be recovered as described hereinafter. The storage tank is constructed of stainless steel, insulated, and heated by a steam coil.

A conventional batch still or column called the dibasic acid batch column serves to remove free water from the aqueous dibasic acids, then convert the succinic and glutaric acids to their respective anhydrides, and then rectify and dibasic anhydrides thus formed into commercially pure products. The aqueous dibasic acids from the dibasic acid storage tank are charged batchwise into the boiler of the batch column following completion of the previous batch run. The boiler is a stainless steel tank containing electrical resistance heaters to allow relatively high temperatures without using high pressure steam or Dowtherm. The column consists of a steel pipe 18 feet tall, packed with Raschig rings. Distillate is condensed in a tube and shell heat exchanger with the process stream on the tube side. The wide range of properties of the distillate requires that the cooling media have a wide range of characteristics. During the precut removal of water and lights, single pass cooling is accomplished with cooling water. When the succinic anhydride cut is approached, cooling water is cut off and air cooling is substituted, using a temperature actuated solenoid valve to control air flow to the heat exchanger.

The dibasic acid batch column is designed to operate at pressures ranging from atmospheric to 10 mm. Hg absolute and at reflux ratios ranging from 0 during water removal to about 5/1 near the cut points. An air bleed valve into reboiler is provided to minimize tendency of high-boiling material to bump under conditions of high vacuum. Vacuum is provided for the column by an electrically driven oil sealed pump with the condensable vapors removed upstream from the vacuum pump by a refrigerated cold trap. The cold trap is drained into the batch neutralization tank after each cycle, during the period of atmospheric pressure operation of the column. Reflux is controlled in the batch column by a tilting cup reflux splitter. The distillate from the column is manually directed to the appropriate receiver by valved pipes with each receiver vented through the cold trap to the vacuum system. Three stainless steel receivers are provided for water and lights cut; succinic anhydride product; and glutaric anhydride product.

The dibasic acid batch column is operated as follows. Aqueous dibasic acid mixture from the dibasic acid storage tank is charged to the column amounting to about 7,000 parts, normally on top of about 1,000 parts of "heel" remaining from the previous distillation. The column is heated to the boiling point of the boiler contents by electrical heaters in the boiler. Amount of heat used in the column is controlled by the addition or deactivation of separately switched heaters. Water is started on the reflux condenser and reflux return to column is closed. Water is removed as distillate at atmospheric pressure until overhead temperature increases to 101°–102° C., indicating that most of the water has been removed from the mixture. Cooling water on the condenser is replaced with air. The vacuum pump is then actuated with the vacuum control set at maximum pressure and reflux ratio set at 2/1. The vacuum control setting is steadily reduced until a distillate pressure of 50 mm. Hg also is reached with a reflux ratio of about 2/1. The distillation is continued at 50 mm. Hg absolute until an overhead temperature of 110° C. at 50 mm. Hg absolute is obtained.

When this point is reached, the overhead valving is changed to allow the distillate to flow to the succinic anhydride product receiver. The reflux ratio is reduced to about 1:1 and distillation is continued until overhead temperature reaches 130° C. where reflux ratio is increased to about 2:1. At an overhead temperature of 135° C., the valving is changed to allow distillate to flow to the glutaric anhydride product tank and the vacuum control setting is reduced slowly but steadily until distillate pressure has reached 10 mm. Hg. Reflux ratio is reduced to about 0.3:1 and glutaric anhydride product is removed until overhead temperature reaches about 185° C., indicating the completion of the glutaric anhydride cut.

When the glutaric anhydride cut is completed, heat is removed from the boiler, and the system is allowed to go to atmospheric pressure. The water and lights receiver is pumped to batch neutralization tanks as is the material caught in the cold trap. The succinic and glutaric anhydride product tanks are drained to product delivery vessels. The still bottoms consisting primarily of linear adipic anhydride (62%), catalyst salts (26%), glutaric anhydride (12%) and small amounts of degradation products are withdrawn from the reboiler while still hot to a bottoms receiver. The receiver is an insulated stainless steel tank containing a steam coil for heating. The still bottoms are then dissolved in an agitated stainless steel dissolving tank containing hot 4–7% aqueous nitric acid. In the dissolution tank most of the linear adipic acid anhydride is hydrolyzed to adipic acid and dissolved along with most of the other contents, including the catalyst salts. A relatively small amount of polymeric material does not dissolve. The adipic acid-catalyst solution from the dissolving tank is pumped through a perforate bowl centrifuge to remove the undissolved residues. These residues are plowed batchwise from the centrifuge into plastic bags for disposal in a sanitary landfill.

The centrifugate from the polymer removal operation is pumped to a crystallization tank. Circulating refrigerated methanol from a chiller is circulated through the cooling coils in the crystallization tank until temperature of the mixture reaches 6° C., and the temperature is held there for 30 minutes. The cold slurry containing precipitated adipic acid is pumped to a perforate bowl centrifuge. Adipic acid retained in the centrifuge bowl is rinsed with a small amount of water, then discharged into plastic-lined drums for marketing. The centrifugate, containing the catalyst salts, is pumped through a final cleanup charcoal bed and stored for reuse in the adipic acid plant.

In operation of the present process as described, there are essentially no gaseous air contaminants, and there is no particulate problem because no conventional drying steps are used in recovery of the several valuable products. Thus, the process is an economic means for solving the serious environmental problem involving disposal of adipic acid bleed stream.

EXAMPLE 2

Table I below shows typical amounts of feeds and products from operation of a commercial plant in accordance with the process of Example 1.

TABLE I

| Process Feeds | | Lbs./Day |
|---|---|---|
| Bleed Stream | | 30,000 |
| Water and Stripping Steam | | 11,470 |
| Urea Scrubber Make-up | | 40 |
| Caustic Neutralizer Make-up | | 70 |
| Products | | |
| Purified Aqueous Adipic Acid-Nitric Acid Returned to Adipic Acid Plant | | 11,565 |
| (as adipic acid) | (2,321) | |
| (as nitric acid) | (2,877) | |
| Succinic Anhydride | | 1,096 |
| Glutaric Anhydride | | 3,816 |
| Adipic Acid Reclaimed from Still Bottoms | | 435 |
| Catalyst Solution Reclaimed | | 2,537 |
| (as Cu(NO$_3$)$_2$) | (172.1) | |
| (as V$_2$O$_5$) | (28.7) | |
| (as HNO$_3$) | (103.0) | |

I claim:

1. A process for treating an adipic acid bleed stream obtained in the manufacture of adipic acid by oxidizing with nitric acid a mixture of cyclohexanol and cyclohexanone in the presence of a catalyst consisting of a mixture of copper and vanadium salts, said adipic acid bleed stream consisting mainly of nitric, adipic, glutaric, and succinic acids and said catalyst; the process comprising:
    a. recovering a portion of the adipic acid from the adipic acid bleed stream by chilling the adipic acid bleed stream to precipitate adipic acid and separating the precipitated adipic acid from the residual adipic acid bleed stream;
    b. dissolving said precipitated adipic acid in aqueous nitric acid to produce a solution which is recycled to said manufacture of adipic acid;
    c. maintaining said residual adipic acid bleed stream in aqueous solution by addition of water as required, and stripping nitric acid from said aqueous solution at about atmospheric pressure with steam at a temperature of about 100° to 110° C. while maintaining in said aqueous solution at least 10–25 weight percent of water and a water to nitric acid weight ratio of at least 6, to remove substantially all of the nitric acid therefrom, thereby forming an aqueous nitric acid free mixture of said dibasic acids and said catalyst, which can be safely dehydrated and distilled to produce useful chemicals.

2. The process of claim 1 wherein said nitric acid is stripped from the aqueous residual adipic acid bleed stream with steam while maintaining in said aqueous solution a water to nitric acid weight ratio of at least 8 by addition of water as required.

3. The process of claim 2 wherein the nitric acid and water vapors from the stripping step are fed to a distillation column to produce a substantially pure water distillate and aqueous nitric acid as bottoms.

4. The process of claim 1 wherein the aqueous nitric acid free mixture of dibasic acids obtained from said stripping step is dehydrated to form succinic anhydride and glutaric anhydride, and said anhydrides are batch distilled at subatmospheric pressure.

* * * * *